United States Patent [19]

Hatfield et al.

[11] 4,230,644

[45] Oct. 28, 1980

[54] HALOGENATING REAGENTS

[75] Inventors: Lowell D. Hatfield, Bargersville; Larry C. Blaszczak; Jack W. Fisher, both of Indianapolis, all of Ind.

[73] Assignee: Eli Lilly and Company, Indianapolis, Ind.

[21] Appl. No.: 8,469

[22] Filed: Feb. 1, 1979

[51] Int. Cl.$^3$ .................................................. C07F 9/14
[52] U.S. Cl. ................................... 260/960; 260/986; 544/16; 544/30
[58] Field of Search ................................ 260/986, 960

[56] References Cited

PUBLICATIONS

Harris et al., "J. Chem. Soci.", (1956), 3038.
Foroman et al., "J. Am. Chem. Soci.", vol. 75, (1953) p. 3145.
Ramirez et al., "J. Am. Chem. Soci.", vol. 90, (1968) p. 3507.
Milobedzki et al., "Rocznik Chemie," vol. 6, (1926) p. 67.
Coe et al., "J. Chem. Soci.", (London), pp. 2281–2288, (1954).
Rydon et al., "J. Chem. Soci.", (London), pp. 3043–3056, (1956).

*Primary Examiner*—Anton H. Sutto
*Attorney, Agent, or Firm*—Steven R. Lammert; Arthur T. Whale

[57] ABSTRACT

Novel halogenating agents are derived from triaryl phosphites and chlorine or bromine. They are useful in converting 7-acylamino-3-hydroxy-3-cephem compounds to 7-acylamino-3-halo-3-cephems and the corresponding C-7 imino halide cephem derivatives.

15 Claims, No Drawings

HALOGENATING REAGENTS

BACKGROUND AND SUMMARY OF THE INVENTION

An intensive research effort in the field of cephalosporin antibiotics has produced a number of clinically significant cephalosporin compounds. One of the more recent developments in this area has been the discovery of cephem compounds directly substituted with halogen at the C-3 position. A number of 3-halo-3- cephems have been described by Chauvette in U.S. Pat. Nos. 3,925,372, 4,064,343 and 3,962,227. These potent antibiotic compounds are prepared by halogenation of the corresponding 3-hydroxy-3-cephems. The halogenation of 3-hydroxy-3-cephems to provide 3-chloro and 3-bromo-3-cephems has typically been carried out by reacting the 3-hydroxy-3-cephem compounds with brominating or chlorinating agents including phosgene, oxalyl chloride, thionyl chloride, thionyl bromide and phosphorus halides such as phosphorus trichloride and phosphorus tribromide, usually in the presence of dimethylformamide.

This invention is directed to a novel class of halogenating agents which are useful in preparing 3- halo-3- cephems.

More particularly this invention is directed to highly reactive halogenating compounds having the empirical formula

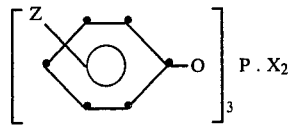

wherein X is Cl or Br and Z is hydrogen, halo, $C_1$–$C_4$ alkyl, or $C_1$–$C_4$ alkoxy, derived from the reaction of a triaryl phosphite and chlorine or bromine respectively.

A number of halogenating agents derived from halogens and phosphorus or phosphorus containing compounds have been described. Known chlorinating and brominating compounds of this type include phosphorus trichloride, phosphorus tribromide, phosporyl chloride, phosphoryl bromide, phosphorus pentachloride, phosphorus pentabromide, triphenyl phosphite dichloride, triphenyl phosphite dibromide, triphenylphosphine dichloride, triphenylphosphine dibromide, catechyl phosphorus tribromide.

Of those prior art compounds, those most closely related to the present compounds are the triphenyl phosphite dihalides which have an empirical formula identical to that of the present compounds. See, for example, D. G. Coe, S. R. Landauer, and H. N. Rydon, J. Chem. Soc., 2281 (1954) and H. N. Rydon and B. L. Tonge, J. Chem. Soc., 3043 (1956). Although both the present triaryl phosphite-halogen compounds and the prior art triaryl phosphite dihalides have identical empirical formulas and are derived generally from the reaction of a triaryl phosphite and chlorine or bromine, physical and chemical data have unequivocally demonstrated the existence of two discrete molecular forms: a kinetic form, described and claimed herein, and a thermodynamically stable form described in the prior art. The halogenating compounds of the present invention have been shown to exhibit marked differences in both physical characteristics and in chemical reactivity when compared with triaryl phosphite dihalides described in the art. Most significantly the triaryl phosphite-halogen compounds of the present invention have been found to be far superior as halogenating agents when compared to the corresponding prior art triaryl phosphite dihalides.

The present compounds are distinguished from the triphenyl phosphite dihalides in the prior art in that the present compounds are the kinetically controlled products of the reaction of a triaryl phosphite and chlorine or bromine; the compounds described in the prior art are the thermodynamically controlled products from the same reactants. In other words the present halogentating compounds can be described as intermediates, previously unrecognized, in the preparation of the prior art triaryl phosphite dihalides from triaryl phosphites and chlorine or bromine.

The present halogenatng compounds can be employed advantageously in the preparation of known 3-halo-3-cephem antibiotic compounds.

DETAILED DESCRIPTION OF THE INVENTION

The present invention is directed to halogenating compounds having the general formula

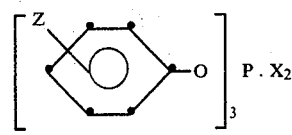

wherein X is Cl or Br and Z is hydrogen, halo, $C_1$–$C_4$ alkyl or $C_1$–$C_4$ alkoxy. These compounds are the kinetically controlled products of the reaction of equivalent amounts of a triaryl phosphite of the formula

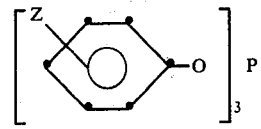

wherein Z is as defined above and bromine or chlorine in a substantially anhydrous inert organic solvent.

The term "halo" in the definition of Z includes chloro, bromo or iodo. "$C_1$–$C_4$ Alkyl" includes methyl, ethyl, ispropyl, n-propyl, n-butyl, sec-butyl, tertbutyl and isobutyl. Representative "$C_1$–$C_4$ alkoxy" groups are methoxy, ethoxy, isopropoxy, t-butoxy, n-butoxy.

The dot (•) in the general formula of the present compounds is used simply to designate that equivalent amounts of halogen and phosphite reagent are combined chemically and in a way that can be distinguished from that in the prior art compounds which typically have been drawn without the dot [e.g. $(PhO)_3PCl_2$]. The exact molecular form of the triaryl phosphite-halogen kinetic complexes described herein has not been established definitely; however physical-chemical data do indicate that the kinetic product is one wherein the phosphorus center acquires some cationic character. Herein the terms "kinetic compound", "kinetic complex," "triaryl phosphite-halogen complex (compound)," "kinetically controlled halogenating compound," and "kinetically controlled product (compound)" are used synonomously and likewise are to be distinguished from those triaryl phosphite dihalides of the prior art.

The term kinetically controlled product is a term of art which, when used in reference to reactions yielding two (or more) products, refers to the product formed faster, regardless of its thermodynamic stability. If such a reaction is stopped well before the products achieve thermodynamic equilibrium, the reaction is said to be kinetically controlled since more of the faster-formed product will be present. In some cases, depending on the rate of formation of the kinetic product and the rate of thermodynamic equilibrium, the kinetically controlled product of a chemical reaction can be prepared and utilized before any significant amount of the product isomerizes to the thermodynamically stable product. It has been discovered that such is the case with the reaction of selected triaryl phosphites and chlorine or bromine in inert organic solvents. Thus, certain triaryl phosphites have been found to react with chlorine or bromine to provide a kinetically controlled product which although thermodynamically unstable, can be generated and utilized advantageously in subsequent reactions. To maximize the production and stability of the kinetically controlled product, reaction conditions are selected so as to minimize the potential for thermodynamic equilibrium of the initial product of the reaction. Most simply conditions for kinetic control are achieved both by lowering the reaction temperature and the temperature of the kinetic product after it is formed, and by minimizing the time allowed for thermodynamic equilibrium, such as by utilizing the kinetic product in a subsequent reaction immediately after it has been prepared.

If a compound of the present invention, prepared from the kinetically controlled reaction of a triaryl phosphite and chlorine or bromine in a substantially anhydrous inert organic solvent, is allowed to stand in solution, it converts to the corresponding thermodynamically stable prior art form at varying rates depending on, among other things, the nature of the triaryl phosphite, the halogen, the solvent and the solution temperature. Thus the reaction of a selected triaryl phosphite and chlorine, for example, in an inert organic solvent can, under selected conditions, be depicted as follows:

Reaction Sequence I

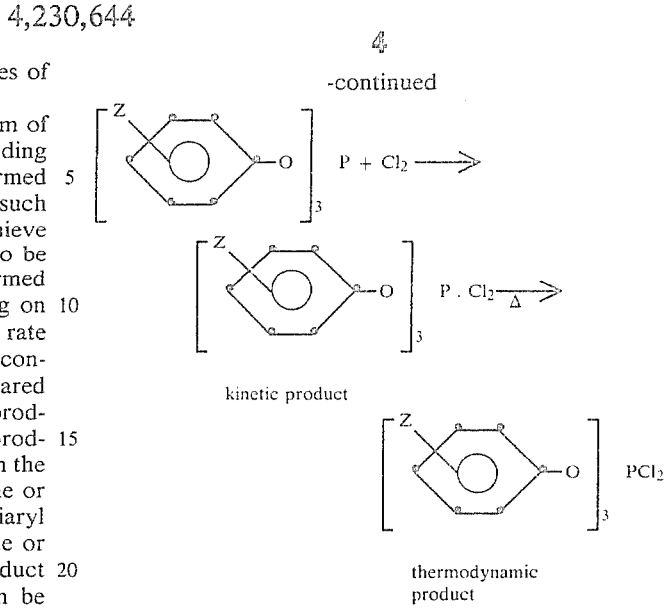

kinetic product thermodynamic product

Experimental data has also shown that the presence of an acid (HX) or an excess of triaryl phosphite will enhance the rate of conversion of the kinetic to the thermodynamic product.

Using $^{31}P$ nuclear magnetic resonance spectroscopy the half-life of the kinetically controlled product from the reaction of triphenyl phosphite and chlorine in methylene chloride at room temperature was determined to be about 8 hours. A half-life of about 39 hours was observed for the triphenyl phosphite-bromine kinetic complex under the same conditions. As mentioned above the observed half-life (rate of conversion) for any given kinetic complex described herein can be affected by the solvent and by the presence of a hydrogen halide acid (HX) or excess triaryl phosphite. Thus for example, a shorter half life will be observed where the solvent for the preparation of kinetic complex has not been rigorously dried; the hydrogen halide acid produced from reaction of the kinetic complex with the moisture present in the solvent will enhance the rate of conversion to the stable form. Table I presents a summary of several properties of the kinetically controlled product and the thermodynamically controlled product of the reaction of triphenyl phosphite and chlorine.

TABLE I

| (See Reaction Sequence I Above) | |
|---|---|
| Kinetic product | Thermodynamic product |
| 1. $^{31}P$ nmr (CH$_2$Cl$_2$) - 3.7 ppm* | 1. $^{31}P$ nmr (CH$_2$Cl$_2$) + 22.7 ppm* |
| 2. $t_{\frac{1}{2}}$ = ≈ 8 hours at room temperature in methylene chloride | 2. Stable at room temperature |
| 3. ir (CH$_2$Cl$_2$) 1120-1190 (vs), 1070 (vs), 1035 (s), 1010 (vs), 990 (vs), 640 (m), 625 (m), 580 (w), 510 (s), 465 (w).** | 3. ir (CH$_2$Cl$_2$) 1130-1210 (vs), 1065 (vs), 1035 (s), 1010 (vs), 980 (vs), 625 (vw), 590 (m), 505 (s) 460 (s).** |
| 4. Hydrolyzes to give HCl and (PhO)$_3$PO | 4. Hydrolyzes to give inter alia HCl, PhOH (phenol) and (PhO)$_2$PCl |
| 5. Reacts with n-BuOH to give HCl, n-BuCl and PhO$_3$PO | 5. Reacts with n-BuOH to give HCl, PhOH (phenol), n-BuCl and (PhO)$_a$(BuO)$_b$ POCl$_c$ wherein a,b,c, = 0$^a$, 1, 2 or 3 and a + b + c = 3 |

*Relative to $^{31}P$ of H$_3$PO$_4$; (+) indicates upfield shift; (−) indicates downfield shift.
**vs = very strong, s = strong, m = medium, w = weak The $^{31}P$ nmr signal for the thermodyamically controlled product was identical to that for the triphenyl phosphite dichloride prepared in accordance with the procedures described in the prior art references referred to hereinabove.

Table II summarizes the $^{31}$P nmr data for several triaryl phosphite dihalide compounds of the present invention.

TABLE II

| Compound | $^{31}$Pnmr-kinetic* (ppm) | half life | $^{31}$Pnmr thermodynamic (ppm) |
|---|---|---|---|
| triphenyl phosphite-chlorine complex | −3.7 | ~8 hours | 22.7 |
| tri(4-methoxyphenyl) phosphite-chlorine complex | −2.2 | >40 hours | — |
| tri(4-chlorophenyl) phosphite-chlorine complex | −6.8 | <1 hour | 23.5 |
| triphenyl phosphite-bromine complex | −3.7 | 39 hours | 22.4 |

*Relative to $^{31}$P of H$_3$PO$_4$ in CH$_2$Cl$_2$

In order to potentiate the formation of the kinetically controlled product the reactants are combined in a substantially anhydrous inert organic solvent at a temperature below about 30° C. Although the present kinetically controlled products are formed at higher temperatures, such conditions favor more the formation of the prior art thermodynamically controlled products. Preferably the halogenating compounds of the present invention are prepared at temperatures at or below about 0°. Minimum reaction temperatures are, of course, determined by the freezing point of the solvent employed for the preparation. Most preferred reaction temperatures are in the range of about −70° to about 0° C.

To minimize the opportunity for equilibration to the less reactive thermodynamic product, the halogenating reagents of the present invention are preferably prepared immediately before they are utilized. Typically the halogenating agent is prepared in the solvent selected for the subsequent halogenation process; the substrate is then simply added to the mixture after the triaryl phosphite-halogen complex of the present invention has been formed.

It has been found that the triaryl phosphite itself reacts to some extent with its kinetic reaction product with chlorine or bromine effectively increasing the rate of conversion to the corresponding thermodynamic product. It is preferred, therefore, but not required, that an excess of halogen be maintained in the reaction mixture during the formation of the present halogenating compounds. This can be achieved practically by adding the triaryl phosphite to a solution of an equivalent amount of the halogen or by adding the halogen and the triaryl phosphite simultaneously to a quantity of an inert organic solvent at the desired temperature. The co-addition of reagents is conducted at such a rate that the color of the halogen persists in the reaction mixture until the last drop of triaryl phosphite discharges the color. Alternatively, excess halogen can be discharged using known halogen scavengers such as acetylenes, or olefins including alkenes, dienes, cycloalkenes, or bicycloalkenes. A preferred scavenger is a C$_2$ to C$_6$ alkene, for example, ethylene, propylene, butylene or amylene.

Attempts to isolate the present halogenating agents simply by evaporation in vacuo of reaction solvent provides a colorless solid which, after being redissolved in CH$_2$Cl$_2$, is shown by $^{31}$P nmr to be a mixture of the kinetically and thermodynamically controlled products and the corresponding triaryl phosphate; the product hydrolyzes to the triaryl phosphate spontaneously when exposed to air in the laboratory.

The kinetically controlled products of the present invention can be stabilized in solution by the addition of about 10 to about 100 mole percent of a tertiary amine base having a pk$_b$ value of about 6 to about 10. If, for example, 50 mole percent of pyridine is added to a solution of the kinetically controlled product of the reaction of triphenyl phosphite and chlorine in methylene chloride, only trace amounts of the thermodynamic equilibrium product can be detected by $^{31}$P nmr, even after prolonged periods at room temperature. The tertiary amine base can be added to a solution of the freshly prepared chlorinating compound or optionally it can be employed in the reaction mixture of the triaryl phosphite and halogen to produce a stabilized solution of the kinetically controlled product of the present invention. Of course, employing such means for stabilizing the present kinetic products allows for the use of higher temperatures for the preparation and storage of the present products.

Suitable triaryl phosphites for the preparation of the present halogenating compound include triphenyl phosphite, tri(p-methoxyphenyl)phosphite, tri(o-chlorophenyl)phosphite, tri(p-chlorophenyl)phosphite, tri(p-tolyl)phosphite, tri(o-tolyl)phoshite, tri(m-bromophenyl)phosphite, tri(p-iodophenyl)phosphite, tri(p-n-propylphenyl)phosphite, tri(p-t-butylphenyl)phosphite, tir(m-tolyl)phosphite, tri(p-isopropoxyphenyl)phosphite and the like. Triphenyl phosphite is preferred primarily because it is commercially available.

Any of a wide variety of inert organic solvents may be employed as the medium for the preparation of the halogenating compounds of the present invention. By "inert organic solvent" is meant an organic solvent which, under the reaction conditions of the preparation and processes of the present invention, does not enter into any appreciable reaction with either the reactants or the products. Since the present halogenating compounds are susceptible to reaction with protic compounds such compounds, including water, alcohols, amines, thiols, organic acids and other such protic compounds should be excluded from the reaction medium.

A substantially anhydrous aprotic organic solvent is preferred. The term "substantially anhydrous," as used in the present description, means that although anhydrous organic solvents are generally preferred, trace amounts of water, such as that often found in commercially available solvents, can be tolerated. Although the kinetic products described herein will react with any water present in the solvent medium, additional amounts of reagents can easily be added to compensate for the loss. It is preferred that conventional laboratory techniques be employed to dry the solvents employed and to exclude moisture from the reaction mixtures.

Suitable solvents include hydrocarbons, both aliphatic and aromatic, including pentane, hexane, heptane, octane, cyclohexane, cyclopentane, benzene, toluene, o-, m- or p-xylene, mesitylene and the like; ethers, cyclic and acyclic such as diethyl ether, butyl ethyl ether, tetrahydrofuran, dioxane, 1,2-dimethoxyethane and the like; carboxylic acid esters such as ethyl acetate, methylformate, methyl acetate, amyl acetate, n-butyl acetate, sec-butyl acetate, methyl propionate, methyl butyrate and the like, nitriles such as acetonitrile, propionitrile butyronitrile and the like; halogenated hydrocarbons, both aromatic and aliphatic, such as chloroform, methylene chloride, carbon tetrachloride, 1,2-dichloroethane (ethylene dichloride, 1,1,2-trichloroethane, 1,1dibromo-2-chloroethane, 2-chloropropane, 1-chlorobutane, chlorobenzene, fluorobenzene, o-, m-, or p-chlorotoluene, o-, m-, or p-bromotoluene, dichlorobenzene and the like; and nitro compounds such as nitromethane, nitroethane, 1-or 2-nitropropane, nitrobenzene and the like.

The particular inert organic solvent employed as a medium for the preparation of the present triaryl phosphite-chlorine complex or as a medium for its use in halogenation processes is not critical, however, such solvent properties as polarity (and therefore substrate solubility) and melting point, and the ease of isolation of the final products may be considered in selecting a most suitable solvent.

Preferred solvents for the preparation of the present compounds are hydrocarbons, especially aromatic hydrocarbons, and halogenated hydrocarbon solvents.

The triaryl phosphite-halogen complexes of the present invention are potent halogenating agents. Like the prior art thermodynamically stable triaryl phosphite dihalide compounds, the present kinetic complexes react with aliphatic alcohols to provide the corresponding alkyl halides (with different by-products). Unlike the prior art triaryl phosphite dichlorides, however, the present compounds efficiently halogenate under mild conditions both enolic groups to form the corresponding vinyl halides and, in the presence of base, amido functions to form the corresponding imino halides.

More particularly the present halogenating complexes can be used in preparing known 3-halo-cephem antibiotics of the formula

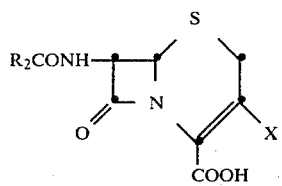

wherein X is chloro or bromo and R₂CO is an acyl group derived from a carboxylic acid, from the corresponding 3-hydroxy cephem compounds. The reaction is conducted in an inert organic solent and is typically carried out at a temperature below about 30° C., preferably at or below 0° C., using about a 10 percent molar excess of both a halogenating compound of the present invention and a tertiary amine base, preferably pyridine. To prevent undesirable side reactions, the C-4 carboxylic acid function of the 3-hydroxy cephem starting materials is protected with one of the conventional carboxylic acid protecting groups. The course of the halogenation can be followed by thin-layer chromatography. The product 3-halocephem compounds can be isolated and purified using conventional laboratory techniques including chromatography, crystallization and recrystallization, filtration and trituration. Removal of the C-4 carboxylic acid protecting group and protecting groups, if any, on the C-7 acylamino group provides biologically active 3-halocephem compounds.

Alternatively, 7-acylamino-3-hydroxy-3-cephems react with about 2 equivalents of a halogenating compound of the present invention in an inert organic solvent in the presence of a tertiary amine base to provide the corresponding 3-halo-3-cephem imino halides of the formula

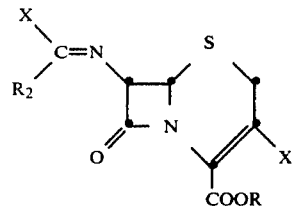

wherein X, R and R₂ are as defined above. The imino halides when treated with a 3–10 fold excess of an alcohol or diol provides 7-amino-3-halo-3-cephem compounds of the formula

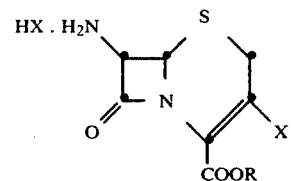

which can be acylated and subsequently deesterified by conventional procedures to provide known 3-halo-3-cephem compounds.

It should be noted that the imino halides of other cephalosporins and penicillins can be prepared from the corresponding 7(or 6)-acylamino derivatives using the present halogenating compounds in the presence of base.

The following examples are provided to further illustrate the present invention. It is not intended that this invention be limited in scope by reason of any of these examples.

EXAMPLE 1

Triphenyl phosphite-bromine kinetic complex.

To a solution of 1.6 gm of bromine in 30 ml of methylene chloride was added a solution of 3.1 gm of triphenyl phosphite in 5 ml of methylene chloride. After warming the product solution to room temperature, it was studied by $^{31}$P nuclear magnetic resonance (nmr). The $^{31}$P nmr spectrum initially indicated 1 major component having a signal at −3.7 ppm relative to the phosphoric acid $^{31}$P resonance signal. This signal decreased in intensity with time as a signal at 22.4 ppm increased in intensity. From the $^{31}$P nmr data the half-life for the initial product was determined to be about 39 hours.

EXAMPLE 2

Triphenyl phosphite-chlorine kinetic complex

Chlorine was added to a solution of 20.0 gm of triphenyl phosphite in 100 ml of methylene chloride at −15° to −20° C. until a faint chlorine color persisted in the mixture. After warming the product solution to room temperature it was studied by $^{31}P$ nmr. The $^{31}P$ nmr spectrum of an aliquot of the product solution initially indicated 1 component having a signal at −3.7 ppm relative to the phosphoric acid $^{31}P$ nmr resonance signal. That signal descreased in intensity with time as a new signal at 22.7 ppm increased in intensity. From the $^{31}P$ nmr data, the half-life for the initial product was determined to be about 8 hours.

EXAMPLE 3

4-Nitrobenzyl 7-phenylacetamido-3-chloro-3-cephem-4-carboxylate

Chlorine was bubbled through a solution of 2.89 ml (11 mmole) of triphenyl phosphite in 50 ml of methylene chloride at −15° C. until the yellow color indicative of excess chlorine persisted. The color was then discharged by the addition of 2 drops of triphenyl phosphite. To the resulting solution of the triphenyl phosphite-chlorine reagent was added 4.54 gm (10 mmol) of 4'-nitrobenzyl 7-phenylacetamido-3-hydroxy-3-cephem- 4-carboxylate and, dropwise over a 40 minute period, a solution of 0.89 ml (11 mmol) of pyridine in 8 ml of methylene chloride. During the pyridine solution addition the temperature of the reaction mixture was maintained at −15° to −10° C. The reaction mixture was then stirred at −15° to −10° C. for an additional 60 minutes after which time the reaction mixture was removed from the cooling bath. Then 1 ml of conc. HCl was added to the mixture to effect hydrolysis of the small amount of imino chloride which had been formed. After stirring the reaction mixture for 30 minutes at room temperature, the mixture was diluted with 100 ml of 3A ethanol, stirred 15 minutes, and then filtered to provide 2.67 grams (54.7%) of the title product as white crystals: m.p. 214° C. (decomp.). A second crop of the title product was obtained by concentrating the filtrate under a reduced pressure to a volume of about 50 ml. An additional 1.52 grams (31.1%) of the title product was isolated. Total yield —85.8%.

nmr (DMSO d-6) δ 3.62 (s, 2), 3.94 (ABq, 2, J=18 Hz), 5.3 (d, 1, J=5 Hz), 5.52 (s, 2), 5.82 (q, 1, J=5 and 8 Hz) and 7.2–8.4 (ArH).

Anal calcd for $C_{22}H_{18}N_3O_6SCl$: C, 54.16; H, 3.72; N, 8.61; Cl, 7.27; S, 6.57.

Found: C, 53.91; H, 3.92; N, 8.44; Cl, 7.27; S, 6.55.

EXAMPLE 4

4'-Nitrobenzyl 7-phenoxyacetamido-3-chloro-3-cephem-4-carboxylate

Following the procedure of Example 3 the triphenyl phosphite-chlorine reagent was prepared from 6.31 ml of triphenylphosphite and chlorine in 45 ml of methylene chloride at −15° C. To this solution at −15° to −10° C. 5.24 gm (10 mmol) of 4'-nitrobenzyl 7-phenoxyacetamido-3-hydroxy-3-cephem-4-carboxylate was added and washed into the reaction mixture with 5 ml of methylene chloride. Then 1.01 ml (12.5 mmol) of pyridine in 8 ml of methylene chloride was added dropwise to the solution over a 30 minute period. After stirring the reaction mixture for 2 hours at −10° C. 1 ml of conc. HCl was added. After stirring an additional 30 minutes the reaction mixture was washed with three 100 ml.-portions of water, dried over magnesium sulfate, and evaporated in vacuo to an oil which was subsequently crystallized from 100 ml. of 2B ethanol to provide 4.19 gm (83.2%) of the title product: m.p. 142.5°–146° C.

nmr (CDCl$_3$) δ 3.7 (ABq, 2, J=18 Hz), 4.60 (s, 2), 5.12 (d, 1, J=5 Hz), 5.4 (s, 2), 5.93 (q, 1, J=5 and 9 Hz), and 6.8–8.4 (ArH).

Anal calcd for $C_{22}H_{18}N_3O_7SCl$: C, 52.44; H, 3.60; N, 8.34; S, 6.36; Cl, 7.04.

Found: C, 52.67; H, 3.73; N, 8.12; S, 6.15; Cl, 6.95.

EXAMPLE 5

4'-Nitrobenzyl 7-phenoxyacetamido-3-chloro-3-cephem-4-carboxylate using tri-o-tolyl phosphite dichloride Chlorine gas was bubbled into a solution of 3.91 gm (10 mmol) of tri-o-tolyl phosphite in 45 ml of methylene chloride at −10° C. until a yellow color persisted. The color was discharged by the addition of approximately 0.5 mmol of the phosphite. To the resulting solution at −10° C. was added 5.4 gm (10 mmol) of 4'-nitrobenzyl 7-phenoxyacetamido-3-hydroxy-3-cephem-4-carboxylate which was washed into the solution with 5 ml of methylene chloride. Then 1.01 ml (12.5 mmol) of pyridine was added. After allowing the reaction mixture to stir for 90 minutes at −10° ml of conc. HCl was added to the reaction mixture. After stirring for an additional 30 minutes the reaction mixture was washed successively with two 25 ml portions of water and 25 ml of dilute soldium chloride solution, dried over sodium sulfate, and evaporated in vacuo to an oil which crystallized from 50 ml. of 2B ethanol to provide 3.35 gm (66.5%) of the title product. An nmr spectrum of the product was identical to that of the product obtained in Example 4.

EXAMPLE 6

4'-Nitrobenzyl 7-phenoxyacetamido-3-bromo-3-cephem-4-carboxylate. Triphenyl phosphite-bromine complex To a solution of 2.30 ml (4.5 mmol) of bromine in 90 ml of methylene chloride at −70° C. was added 12.22 ml (46.6 mmol) of triphenyl phosphite to discharge the bromine color. To this solution was added 10.6 gm (20 mmol) of 4'-nitrobenzyl 7-phenoxyacetamido 3-hydroxy-3-cephem-4-carboxylate which was washed into the reaction mixture with 10 ml of methylene chloride. The mixture was warmed to −35° to −30° C., and a solution of 3.64 ml (45 mmol) of pyridine in 16 ml of methylene chloride was added dropwise over 35 minutes. After 4 hours 50 ml of ice-water was added to the reaction mixture. The resulting solution was stirred for ½ hour. Three layers were noted. The methylene chloride layer, the middle layer, was washed with 50 ml of water and brine and then dried with anhydrous Na$_2$SO$_4$. The solvent was evaporated in vacuo to a weight of 29.7 grams. The addition of 150 ml of methanol induced crystallization of the titled product (3.78 g): m.p. 138°–139° C.

nmr (DMSOd-6) δ4.0 (ABq, C$_2$—H), 4.65 (s, 2, side chain CH$_2$), 5.28 (d, 1, J=5Hz), 5.47 (s, 2, ester Ch$_2$), 5.8 (q, 1, J=5Hz and 8Hz) and 6.9 8.4 (ArH)

EXAMPLE 7

4'-Nitrobenzyl 7-amino-3-methyl-3-cephem-4-carboxylate, hydrochloride

(A) From 4'Nitrobenzyl 7-phenoxyacetamido-3-methyl-3-cephem-4-carboxylate

A solution of the triphenyl phosphite-chlorine reagent was prepared by bubbling chlorine through a solution of 2.89 ml (11 mmol) of triphenyl phosphite in 50 ml of methylene chloride at −15° C. To this solution was added 5.02 gm (10 mmol) of 4'-nitrobenzyl 7-phenoxy-acetamido-3-methyl-3-cephem-4-carboxylate and 0.85 ml (11.5 mmol) of pyridine. The reaction mixture was stirred for 1 hour at −15° to −10° C. after which time was added 6.0 ml (64.8 mmole) of isobutanol. The cooling bath was removed, and the reaction mixture was allowed to warm to room temperature over a 2 hour period. The titled nucleus hydrochloride ester, which began to crystallize in about 15 minutes, was filtered, washed with methylene chloride, and dried. A total of 3.55 grams (92%) of the titled product was obtained as white crystals: m.p. 189° C. (decomp.).

(B) From 4'-Nitrobenzyl 7-heptanoylamido-3-methyl-3-cephem-4-carboxylate.

The experimental procedure described in Paragraph A above was repeated in detail using 4.61 gm (10 mmol) of 4'-nitrobenzoyl 7-heptanoylamido-3-methyl-3-cephem-4-carboxylate as the substrate. A total of 6.32 gm (93.8%) of the nucleus ester hydrochloride as snow white crystals was isolated: m.p. 188.5° C. (decomp.).

(C) From 4'-Nitrobenzyl 7-phenoxyacetamido-3-methyl-3-cephem-4-carboxylate in tetrahydrofuran A solution of the triphenyl phosphite-chlorine reagent was prepared by bubbling chlorine into a solution of 11 mmol of triphenyl phosphite in tetrahydrofuran (THF) at −10° C. To the solution was added 4.84 gm (10 mmol) of 4'-nitrobenzyl 7-phenoxyacetamido-3-methyl-3-cephem-4-carboxylate. Subsequently 0.95 ml (11 mmol) of pyridine was added to the reaction mixture. The reaction was then allowed to stir at −10° C. for 1 hour after which time it was allowed to warm to room temperature and stir for another 2 hours. Then 6.0 ml (65 mmol) of isobutanol was added. After 2 hours the reaction mixture was filtered. The crystalline nucleus hydrochloride ester thereby obtained was washed with THF and dried affording 3.03 gm (78.5%): m.p. 151–153° C. (decomp.).

(D) From 4'-Nitrobenzyl 7-phenoxyacetamido-3-methyl-3-cephem-4-carboxylate in acetonitrile A solution of the triphenyl phosphite-chlorine reagent was prepared by bubbling chlorine into a solution of about 11 mmol of triphenyl phosphite in 45 ml of acetonitrile at −10° C. To this solution was added 4.84 gm (10 mmol) of 4'-nitrobenzyl 7 -phenoxyacetamido-3-methyl-3-cephem-4-carboxylate and subsequently 0.95 ml (11 mmol) of pyridine at −10° C. After the reaction mixture was allowed to stir for 2 hours at −10° C. the ice bath was removed. After an additional 2 hours, 6.0 ml (65 mmol) of isobutanol was added to the reaction mixture. With seeding the product crystallized, and after stirring for 1 hour, it was filtered, washed with acetonitrile, and dried. Total yield 2.55 gm (66 .1%): m.p. 184° C. (decomp.).

(E) From 4'-Nitrobenzyl 7-phenoxyacetamido-3-methyl-3-cephem-4-carboxylate in ethyl acetate The same procedure was followed as described in Paragraph D above except that ethyl acetate was used as a solvent for the triphenyl phosphite-chlorine kinetic product formation and for the cleavage process. Total yield 2.48 grams (64.2%): m.p. 177°–179° C. (decomp.).

(F) From 4'-Nitrobenzyl 7-phenoxyacetamido-3-methyl-3-cephem-4-carboxylate using tri-o-tolyl phosphite-chlorine.

A solution of tri-o-tolyl phosphite-chlorine reagent was prepared as follows: 3.91 gm (11 mmol) of tri-o-tolyl phosphite was added to 45 ml of methylene chloride and cooled to −10° C. under a nitrogen atmosphere. Chlorine gas was bubbled into the solution until the yellow color persisted. Then about 0.5 mmol of tri-o-tolyl phosphite was added to discharge the yellow color. To the solution was added 4.84 gm (10 mmol) of 4'- nitrobenzyl 7 -phenoxyacetamido-3-methyl-3-cephem-4-carboxylate and 1.01 ml. (12.5mmol) of pyridine. The reaction mixture was removed from the cooling bath and stirred for 90 minutes after which time 5.1 ml (55 mmol) of isobutanol was added. The product began to crystallize about 5 minutes after gaseous HCl was bubbled into the reaction mixture. After 90 minutes the reaction mixture was filtered. The product was washed with 25 ml. of methylene chloride and dried at reduced pressure. Total yield—3.46 grams (89.6%): m.p. 184° C. (decomp.).

(G) From 4'-nitrobenzyl 7-phenoxyacetamido-3-methyl-3-cephem-4-carboxylate using tri(p-methoxyphenyl) phosphite-chlorine complex.

A solution of tri(p-methoxyphenyl)phosphite chlorine complex was prepared as follows: A solution of 4.6 grams (11.5 mmol) of tri(p-methoxyphenyl)phosphite in about 5 ml. of methylene chloride was added dropwise to 45 ml of methylene chloride at −10° to −20° C. with simultaneous addition of chlorine to a colorless endpoint. After the addition of all of the phosphite reagent, additional chlorine was added to give a faint yellow color; the color of excess chlorine rapidly dissipated without adding more phosphite. To the resulting solution was added 4.84 gm (10 mmol) of 4'-nitrobenzyl 7-phenoxyacetamido-3-methyl-3-cephem-4-carboxylate which was washed into the reaction mixture with 5 ml of methylene chloride. Subsequently a solution of 1.01 ml of pyridine (12.5 mmol) in 4 ml of methylene chloride was added dropwise to the reaction mixture over a 15 minute period. After stirring the reaction mixture for 15 minutes at −10°, 5.1 ml. of isobutanol (55 mmol) was added to the reaction mixture. HCl gas was bubbled into the reaction mixture, and shortly thereafter the cooling bath was removed. After 2 hours at room temperature the reaction mixture was filtered to provide 0.89 grams (23%) of the nucleus hydrochloride ester: m.p. 173°–174° C.

EXAMPLE 8

2',2',2'-Trichloroethyl 7-amino-3-methyl-3-cephem-4-carboxylate, hydrochloride, in benzene (A) Chlorine gas and 3.16 ml (12 mmol) of triphenylphosphite were added simultaneously to 45 ml. of benzene at 10° to 15° C. A slight yellow color was maintained in the reaction mixture until the last drop of phosphite added cleared the solution. To this solution was added 4.64 gm (10 mmol) of 2',2',2'-trichloroethyl 7-phenylacetamido-3-methyl-3-cephem-4-carboxylate. After stirring the reaction mixture for 5 minutes at 10° to 15° C. a solution of 1.01 ml (12.5 mmol) of pyridine in 8 ml of benzene was added over 15 minutes. After stirring the reaction mixture for a total of 45 minutes, 5.1 ml (55 mmol) of isobutanol were added and HCl was bubbled into the reaction mixture for about 90 seconds. The titled product crystallized while the reaction mixture was stirred at room temperature for a period of 2 hours. Filtration provided 3.5 gm (91.6%) of titled nucleus ester hydrochloride: m.p. 179° C. (decomp.).

nmr (DMSO d-6) δ2.27 (s, 3), 3.6 (ABq, 2 J=16 Hz), 5.00 (s, 2 ), and 5.12 (q, 2, J=4 Hz, β-lactam H).

(B) The same procedure was followed as described in Example 8 Paragraph A immediately hereinabove except that all preparations were conducted as room temperature (20°-25° C.) instead of 10°-15° C. A total 3.26 gm (85.4%) of the titled nucleus ester hydrochloride was isolated: m.p. −179° C. (decomp.).

EXAMPLE 9

4'-Nitrobenzyl 7-amino-3-methyl-3-cephem-4-carboxylate hydrochloride using tri (p-chlorophenyl)phosphite-chlorine kinetic complex To 5.17 g (12.5 mmol) of tri(p-chlorophenyl) phosphite and 0.27 ml (3.28 mmol) of pyridine in 25 ml of methylene chloride at −70° C. was added chlorine gas. Amylene (0.40 ml) was added to discharge excess chlorine. To the resulting solution were added 4'-nitrobenzyl 7-phenoxyacetamido-3-methyl-3-cephem-4-carboxylate (2.42 gm, 5 mmol) and pyridine (0.79 ml, 9.22 mmol) in 4 ml of methylene chloride dropwise over 11 minutes. After 3 hours the cooling bath was removed and 6.94 ml of isobutanol was added. After the reaction mixture had warmed to about −10° C., HCl gas was bubbled into the mixture for about 1 minute. After 15 minutes the reaction mixture was filtered to give 1.86 gm (96%) of the titled product as a white solid, m.p. 184°-185° C. (decomp).

EXAMPLE 10

4'-Nitrobenzyl 7-amino-3-chloro-3-cephem-4-carboxylate hydrochloride using tri(p-chlorophenyl)phosphite-chlorine kinetic complex To 10.34 gm of tri(p-chlorophenyl)phosphite and 0.53 ml (6.5 mmol) of pyridine in 50 ml of methylene chloride at −70° was added chlorine in 15 ml of methylene chloride. Amylene (0.52 ml) was added to discharge excess chlorine. To the resulting solution of the tri(p-chlorophenyl)phosphite-chlorine complex was added 4'-nitrobenzyl 7-phenoxyacetamido-3-hydroxy-3-cephem-4-carboxylate (5.28 gm) using 10 ml of methylene chloride to wash the substrate into the reaction mixture. Then 1.57 ml (19.5 mmol) of pyridine in 9 ml of methylene chloride was added dropwise over 33 minutes. After 2 hours the reaction mixture was allowed to warm to 2° C. Isobutanol (6.94 ml) was added, and HCl gas was bubbled through the mixture for 2 minutes. The mixture was evaporated in vacuo to a syrup to which was added 50 ml of ethyl acetate. The gum was triturated with about 100 ml of ethanol. A white solid, tri(p-chlorophenyl)phosphate, was filtered. The filtrate was evaporated in vacuo to dryness. To the residue was added 15 ml of 1:1-toluene/ethyl acetate and just enough methanol to dissolve the gummy residue. Upon standing for about 5 minutes, 0.97 gm of the titled product crystallized as a white solid. m.p. 184°-186° C. (decomp).

We claim:

1. A halogenating compound of the general formula

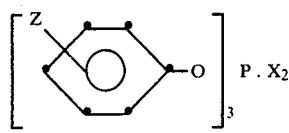

which is the kinetically controlled product of the reaction of equivalent amounts of a triaryl phosphite of the formula

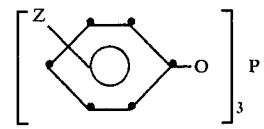

and chlorine or bromine in a substantially anhydrous inert organic solvent wherein in the above formulas Z is hydrogen, halo, $C_1$-$C_4$ alkyl or $C_1$-$C_4$ alkoxy, and X is Cl or Br.

2. The compound of claim 1 wherein Z is hydrogen, methyl or methoxy.

3. The compound of claim 1 wherein Z is hydrogen.

4. The compound of claim 1 wherein X is Cl.

5. The compound of claim 1 wherein X is Br.

6. The compound of claim 1 prepared at a temperature at or below about 0° C.

7. The compound of claim 6 wherein an excess of chlorine is maintained during the reaction of the triaryl phosphite and chlorine.

8. The compound of claim 7 prepared using an aromatic hydrocarbon or halogenated hydrocarbon solvent.

9. The compound of claim 8 prepared at a temperature of about −70° to about 0° C.

10. The compound of claim 6 prepared using an aromatic hydrocarbon or halogenated hydrocarbon solvent.

11. The compound of claim 6 wherein an excess of bromine is maintained during the reaction of the triaryl phosphite and chlorine.

12. The compound of claim 11 prepared using an aromatic hydrocarbon or halogenated hydrocarbon solvent.

13. The compound of claim 12 prepared at a temperature of about −70° to about 0° C.

14. A compound having the empirical formula

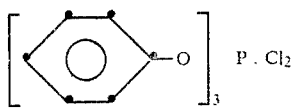

which (a) has a $^{31}P$ nuclear magnetic resonance signal in methylene chloride at $-3.7$ ppm relative to that of phosphoric acid;

(b) has in, methylene chloride, an infrared spectrum which exhibits the following characteristic absorptions: 1120–1190 (very strong), 1070 (very strong), 1035 (strong), 1010 (very strong), 990 (very strong), 640 (medium), 625 (medium), 580 (weak), 510 (strong) and 465 (weak);

(c) reacts with water to give HCl and triphenyl phosphate; and (d) reacts with n-butanol to give HCl, n-butyl chloride, and triphenyl phosphate.

15. A compound having the empirical formula

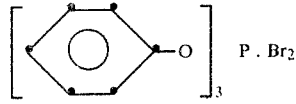

which has a $^{31}P$ nuclear magnetic resonance signal in methylene chloride at $-3.7$ ppm relative to that of phosphoric acid.

* * * * *